US009528975B2

United States Patent
Silva Ferreira et al.

(10) Patent No.: US 9,528,975 B2
(45) Date of Patent: Dec. 27, 2016

(54) NON-DESTRUCTIVE AND NON-INVASIVE METHOD FOR INSPECTING VEGETABLE MATERIALS INVOLVING THE USE OF ELECTROMAGNETIC RADIATION

(75) Inventors: António César Silva Ferreira, Paio de Oleiros (PT); Francisco Manuel Couto Oliveira, Paio de Oleiros (PT); Ana Cristina De Avelar Lopes Cardoso Mesquita, Paio de Oleiros (PT)

(73) Assignee: Cork Supply Portugal, S.A., São Paio de Oleiros (PT)

( * ) Notice: Subject to any disclaimer, the term of this patent is extended or adjusted under 35 U.S.C. 154(b) by 263 days.

(21) Appl. No.: 13/518,047

(22) PCT Filed: Dec. 9, 2010

(86) PCT No.: PCT/PT2010/000058
§ 371 (c)(1),
(2), (4) Date: Jun. 21, 2012

(87) PCT Pub. No.: WO2011/078714
PCT Pub. Date: Jun. 30, 2011

(65) Prior Publication Data
US 2013/0163720 A1    Jun. 27, 2013

(30) Foreign Application Priority Data
Dec. 21, 2009   (PT) .......................... 104902

(51) Int. Cl.
    G01N 23/02    (2006.01)
    G01N 33/46    (2006.01)
    G01N 23/04    (2006.01)
(52) U.S. Cl.
    CPC ............ *G01N 33/46* (2013.01); *G01N 23/046* (2013.01); *G01N 2223/419* (2013.01)

(58) Field of Classification Search
    CPC ........ G01N 23/00; G01N 23/02; G01N 23/04; G01N 23/06; G01N 23/18
    USPC ................................................ 378/51, 58, 62
    See application file for complete search history.

(56) References Cited

U.S. PATENT DOCUMENTS

| 6,597,761 | B1 | 7/2003 | Garms, III |
| 2004/1057551 | | 3/2004 | Skatter |

FOREIGN PATENT DOCUMENTS

WO    WO 2007/026233    3/2007

OTHER PUBLICATIONS

Brunetti A et al: "Cork quality estimation by using Compton tomography", Nuclear Instruments & Methods in Physics Research, Section-B:Beam Interactions With Materials and Atoms, Elsevier, Amsterdam, NL, vol. 196, No. 1-2, Nov. 1, 2002, p. 161-168.
International Search Report for International Application No. PCT/PT2010/000058 mailed Apr. 19, 2011.
(Continued)

*Primary Examiner* — Jurie Yun
(74) *Attorney, Agent, or Firm* — Pearl Cohen Zedek Latzer Baratz LLP

(57) ABSTRACT

This invention describes a method to monitor intrinsic parameters of natural cork stoppers, based on a non-invasive and non-destructive method, e.g. X-Ray spectroscopy, so that objects (stoppers) can be segregated and categorized according to the relation of such parameters with relevant characteristics for the performance of the closure, as, for instance, gas permeability. This invention does also describe how the information about physical and chemical parameters of the cork is processed directly from the data acquired in the production line.

6 Claims, 7 Drawing Sheets

(56) References Cited

OTHER PUBLICATIONS

ASTM F 1307-02. "Standard method for oxygen transmission rate through dry packages using a coulometric sensor," EDT 2006.

Casey, J.A., "Venting or Leaking? Residual Headspace Pressure in Bottled Wines," A&NZGG&WM (The Australian & New Zealand Grapegrower & Winemaker), vol. 453, pp. 115-118, Aug. 2001.

Crochiere, G. K.; "Measuring Oxygen Ingress During Bottling/Storage". Practical Winery & Vineyard, Jan./Feb. 2007.

Ferreira, A.C. et al., "Identification of Key Odorants related to the typical aroma of oxidation-spoiled white wines," J. Agric. Food Chem. 2003, vol. 51, pp. 1377-1381.

Ferreira, A. C. et al., Kinetics of oxidative degradation of white wines and how they are affected by selected technological parameters, J. Agric. Food Chem. vol. 2002, No. 50, pp. 5919-5924.

Hart and Kleinig. "The role of oxygen in aging of bottled wine," The Australian & New Zealand Grapegrower & Winemaker, 2005, vol. 20, pp. 46-50.

Heald, Eleanor et al., "Getting Closure. The continuing search for the best way to seal the bottle," Jan. 18, 2008. <http://www.appellationamerica.com/wine-review/532/Nomacorc-research.html>.

Kwiatkowski, M. J. et al; "The impact of closures, including screw cap with three different headspace volumes, on the composition, colour and sensory properties of a Cabernet Sauvignon wine during two years' storage." Australian Journal of Grape and Wine Research, 13, 81-94, 2007.

Lopes, P. et al., "Impact of storage position on oxygen ingress through different closures into wine bottles," Journal of Agricultural and Food Chemistry, 2006, vol. 54, No. 18, pp. 6741-6746.

Lopes, P. et al. "Nondestructive colorimetric method to determine the oxygen diffusion rate through closures used in winemaking," Journal of Agricultural and Food Chemistry, 2005, vol. 53, pp. 6967-6973.

Phillips, C.; "Recent Research: The Science of Closures," From Wine Business Monthly, Sep. 15, 2005, www.winebusiness.com.

Tran, T., et al., "Using Membrane Technology to Optimise Closure Performance," The Australian & New Zealand Grapegrower & Winemaker, Mar. 2007, pp. 59-60, 62.

Tudor, P., "Is This the Closure for Your Wine? An in-depth look at the pros and cons of wine development under screw caps." Wine Business Monthly, Jul. 2005.

Waters, L., et al., "Wine and Oxygen Research at the AWRI," Jan. 2008, Sacramento, CA.

NON-DESTRUCTIVE AND NON-INVASIVE METHOD FOR INSPECTING VEGETABLE MATERIALS INVOLVING THE USE OF ELECTROMAGNETIC RADIATION

CROSS-REFERENCE TO RELATED APPLICATIONS

This application is a National Phase Application of PCT International Application No. PCT/PT2010/000058, International Filing Date Dec. 9, 2010, claiming priority of Portuguese Patent Application No. 104902, filed Dec. 21, 2009, which is hereby incorporated by reference.

SCOPE OF THE INVENTION

The present invention concerns a non-destructive and non-invasive method to inspect plant materials, based on the use of electromagnetic radiation, comprising the steps of inspecting and classifying plant material, preferably cork stoppers. Such classification is performed in different categories of one same property such as gas permeability, presence of defects or different densities. In particular, the specific parameter to be quantified is the presence of structures of different optical densities related to the presence of defects in the plant material.

These parameters are obtained by processing a signal acquired by a non-invasive and non-destructive technique as X-Rays, which originates a mathematical model applied to the intended categorisation. The mathematical model is calibrated by processing the property data to be inspected over known samples.

The said mathematical model is constructed on a group of previously selected samples, based on the following variables: one matrix containing the value of the parameter to be calibrated—obtained by classical or normalised methods—and another matrix containing the signal obtained from the X-Ray image.

The mathematical model is later used in said categorisation by means of the signal acquired by the sensor in the productive process of inspecting new samples, the expected value for the intended parameter being then calculated.

The categorisation may be done according to such perspectives as:

(i) Rejection of groups that may not comply with the intended parameter by inspection and processing according to the adopted model (ii) Acceptance of a group corresponding to the criteria established in the adopted model (iii) Categorisation in groups of estimated property or properties.

BACKGROUND OF THE INVENTION

Processing cork and stoppers undergoes a continuous and careful visual quality selection. However, this is essentially based on the appreciation of the surface through visual inspection or photographic means, the presence of possible internal structural defects being yet to clarify. This fact renders it impossible to fully eliminate those stoppers that will not comply with their sealing function (for liquids and gases).

On the other hand, although preventive and curative processes have been developed by the cork industry to minimize the transference of compounds with an impact on taste, namely residues of chloroanisoles, there has been no technical or scientific activity towards improving or classifying the performance in respect of gas transference behaviour, e.g. oxygen.

Science literature frequently refers to the differences among cork stoppers and to their comparison with alternative systems (Crochiere, 2007; Kwiatkowski, 2007; Tran, 2007; Waters, 2007), but no attention has been drawn to optional segregation or manipulation practices regarding the gas transference behaviour, particularly in the case of cork stoppers.

The available results on the most recent research applied to the sealing of wine bottles do essentially outline the following aspects:

1st. Development of methods to measure oxygen permeability

2nd. Comparative study of different systems for sealing wine bottles

3rd. Sealing systems contribution to manage oxygen in the cellar, namely as a predicting tool for the wine's shelf-life in the market.

However, the applicants have no knowledge of any practical application of the performed researches in respect of improving the performance of cork stoppers.

On the other hand, at the level of methods developed to measure permeability, we have no knowledge of any non-destructive and non-invasive applications, which, primarily, may prove to result in a tool for the segregation of stoppers, based on their permeability, before they are really used.

In what concerns the interpretation of the gas diffusion and permeation phenomena, considering the characteristics of cork, the application of the principles of the conventional dynamics of fluids, wherein parameters such as density, pressure, temperature and flow of the particles are well defined in a determined point, is not feasible.

Considering its porous structure, the oxygen transportation regime is fundamentally conditioned by the average free trajectory[1] of the means, the use of statistic mechanics being advisable.

It is within this scope that the novelty and pertinence of the present invention fits:

1. Constitute a data base that may allow the classification of the cork stopper in function of its structural and functional characteristics 2. Allow the identification of stoppers that shall not provide an effective sealing, namely the occurrence of structural defects;

3. Allow the classification of stoppers with different oxygen permeability;

4. Develop a classification methodology permitting their separation in order to place in the market lots with functional predictability.

DESCRIPTION OF THE INVENTION

Field of the Cork Stopper and Function Thereof

The industrially applicable cork is a material of plant origin constituted by cells formed by the traumatic phellogen that covers the cork-oak trunk (species Quercus sober). After their formation such cells have walls/membranes and cytoplasm but, after the cells death the cytoplasm residues are deposited on the inner face of the cell wall and are readsorbed or incorporated in the secondary wall (Amaral Fortes, 2004).

Considering the high number of variables and parameters (factors that are inherent to climate, to intra and inter-annual cell formation and are also related to the genetics of the tree)

at stake, characteristic of a heterogeneous natural product, the predictability of the behaviour and performance of the cork stopper becomes impossible, without recourse to tools that may capture in holistic form (therefore, integrated) the maximum heterogeneity/complexity, in a non-destructive way, for later classification.

The normalisation activity of the raw-material does not, therefore, constitute an option for the sector. Nevertheless, the growing demand of cork stoppers users/consumers, who require a reliable and predictable product, leads to a very serious consideration on developing techniques that may permit the separation of the produced individuals (cork stoppers) according to their expected behaviour in relation with parameters such as gas permeability, presence of defects (namely those which cannot be seen at the surface) or density.

Only in this way shall it be possible to keep up with the competition of alternative synthetic closures which technological nature is considerable easier to control.

Field of the Cork Sector

Traditionally, cork has been used in the form of a stopper to seal bottles of drinks, the most important application being its use for preserving wines. A natural cork stopper has unique physical properties as it is resilient, hydrophobic and impervious both to gas and liquids, which no other natural or artificial product has, until today, been able to match. In addition to an effective sealing, these properties ensure a suitable maturation or ageing of the wine and, hence, it is frequently used in high quality wines that are stored for long periods of time (Fischer, 1997; Insa, 2006).

However, this application is being threatened because of some reliable options that appeared as an alternative to this system of sealing wine bottles. The said alternative systems have taken a position in respect of the cork stopper as guaranteeing sensory and functional consistency, namely in what concerns the transference of compounds that may alter the organoleptic characteristics of the former, as well as regularity and predictability in respect of gas transferences between the outside of the bottle and the product contained therein.

Thus, it may be considered that the apparent inconsistency of the cork product is related to considerable losses in the wine industry. On the other hand, the inexistence of a suitable technical response permitted that those same alternative sealing systems gain a market share, to the detriment of the cork stopper in spite of its countless technical, ecological and social advantages.

The expected functionality of wine bottle stoppers is mainly their sealing capacity, innocuity and sensory neutrality.

In the case of cork stoppers production, the basis is a product of plant origin, the characteristics of which are related with a network of factors of biologic, genetic and climatic nature. Industrial transformation seeks, on its turn, to obtain a product of constant quality, adopting productive practices capable of overcoming the aforementioned variability and allowing the supply of a product with predictable characteristics in what concerns the capacity of preserving the quality of the bottled wine. Therefore, it should be borne in mind that, as we are dealing with a natural product, the field of technical aspects reaches its limits when the heterogeneity of the proper material has to be accepted, without detriment of the desired general functionality, because no stronger technological resources exist.

The introduction of the technology described in this invention, based on information contained in the cork and presently inaccessible, allows the production management of cork stoppers based on objective parameters. The acquired information permits the following:

predict the functional behaviour of the cork stopper in a bottle within parameters such as permeability, presence of defects and density lower the heterogeneity of a certain lot, by separating elements of distinct characteristics within the mentioned parameters improve functional guarantees before customers add a commercial value to the product.

Relevance in Functionality of the Cork Closure

One of the functions that are yet to be controlled in cork closures is their gas permeability, namely oxygen, and especially in the perspective of their use in glass bottles.

Oxygen has a primary role in the product's (wine) lifetime. Hence, its control in the packaging determines the product's longevity in the market which, for the wine sector, is a critical factor. In fact, the "oxidative degradation" of wines does rapidly result in a strong loss of the wine's sensory qualities. From an aromatic point of view, this phenomenon means a loss of flavours that are a characteristic of new wines, such as "floral" and "fruity" and, in parallel, the appearance of aromatic notes proper to older wines and/or atypical flavours associated with the product's deterioration. From a chromatic point of view there is the development of a brownish colour, called "non-enzymatic browning". However, different works stress that the aromatic deterioration precedes the chromatic one (WIDENRADT and SINGLETON 1974; and FERREIRA, et al, 1997).

The bottled product's lifetime or shelf-life is conditioned by the combination of the wine's resistance to oxidation (related to the wine composition in determined substances, particularly the phenolic compounds, and with the pH under which it is stored [WIDENRADT and SINGLETON, (1974), SINGLETON and KRAMLING (1976), and SINGLETON, (1987)]) and the optimal quantity of oxygen ingress through the closure.

However, the cork sector has not yet been able to keep up with this need, which originated the growth of technological (synthetic) alternative options in the market for sealing wine bottles.

This invention intends to contribute to the classification of cork stoppers, e.g. according to their oxygen permeability, presence of defects and/or density. On the other hand, it may also contribute to a significant improvement in the quality control methods used in the cork stoppers sector.

Industrial Inspection

The applications of different electromagnetic regions, starting from what is visible, have been developing since the 19th century for the most diverse technical and scientific purposes. These techniques are very useful because they allow us to 'read' some objects with details that are visually imperceptible, using non-destructive and non-invasive techniques on the material under analysis.

The principle of these applications is based on the fact that the electromagnetic energy, which has a wave nature, undergoes interference, polarisation, refraction, diffraction, reflection, among other effects, when it goes through an object.

Nowadays, there are several applications of non-invasive and non-destructive methods based on the use of electromagnetic radiation, strongly incident on the medical field and for various scientific and research purposes, some industrial applications having been also developed. The possibility of obtaining information through non-invasive and non-destructive means is a present concern which reflects the strong development of process analytical technology (PAT) in many different fields requiring high levels of safety, assurance and control as, e.g., in the pharmaceutical industry.

Although many analytical options are available (as, e.g., MNR, ultrasound, etc.) the limitations of their application at functional level, i.e., at the sample-detector interface, and at financial level, i.e., investment and operating costs, result in that industrial applications do especially seek support on the use of less costly detection methods such as infra-red and or X-Ray spectroscopy.

The present patent is primarily based on the use of this last radiation because it presents the pretended applicability, as its use in densitometry demonstrates, in addition to the perfect mastering and mature knowledge of the technology.

The strategy described in acquiring and processing the signal may, however, be used with other techniques for the acquisition of signal.

X-Rays are electromagnetic emissions the wave length of which varies between $5e^{-3}$ to 1 nm and the photons energy is in the range of tens or hundreds of keV. This electromagnetic energy is generated by the transition of electrons in the atoms, or deceleration of charged particles.

Like all electromagnetic energy of wave nature, X-Rays undergo interference, polarisation, refraction, diffraction, reflection. Interference is used in medicine to obtain images which information, when placed within the context of an anatomic plan, permits the detection of anomalies. This principle of pattern detection in the internal structure of one tissue is not restrained to the clinical area and is generally used in different objects of biological or other origin. In fact, the density of the material may be determined by the relationship between the radiation that is issued and the one that is absorbed, an example of which being the bone densitometry in medical care.

The most relevant aspects of this analysis are its non-destructive and non-invasive characteristics, which permit a high-resolution structural study that may reach a molecular level, e.g. the protein structure, by X-Ray molecular diffraction.

The inherent complexity of biological systems is translated in a complete heterogeneity in the phenotype, i.e., the form and function of different tissues, as is the case of the plant tissue cork. In this way, its use for industrial purposes, which normally imply a high resolution classification at the level of specifications for physical and chemical properties, becomes highly difficult and susceptible of error. Thus, obtaining this information in a non-invasive and non-destructive mode is an indispensable condition for the rigorous classification of the object.

X-Ray radiation, for the above mentioned characteristics, justify its selection as the methodology for analysing and inspecting biological material. In fact, images acquired by this process, contain sufficient structural information for a robust classification of the material.

The visible patterns in the 2D image with the respective gradients of grey translate the differences in density of the plant material. Darker regions correspond to less resistance and, inversely, lighter regions to more resistance to the radiation.

This image is thus the projection of the 3D object on a 2D space corresponding to the "fingerprint" of the respective resistance against radiation transference.

The development of suitable equipment would permit an "on-line" control, stopper after stopper, similar to the one which is nowadays effected in sorting by visual aspect, by image processing, thus allowing a segmentation by flow subcategories of each natural stopper.

Mathematical Signal Processing

The present invention also describes the adoption of multi-varied mathematical methods to process a signal acquired by a non-destructive and non-invasive spectrometric examination to construct algorithms that permit the following:

1. Detect objects/stoppers for analysis;
2. Pattern recognition related to a certain characteristic to be classified;
3. Classify the same objects according to established criteria.

One of the challenges of the present invention lies at the level of the mathematical processing that permits the decomposition of a signal for the extraction of relevant variables to determine some cork stopper characteristics which may have an impact on their performance in the bottle as, for instance, permeability, presence of defects and/or density, from a data set contained in a complex signal obtained by a non-invasive and non-destructive method as, for example, X-Ray analysis.

Industrial Inspection

Some new measuring techniques have been developed that can be directly applied on on-line samples, particularly in situations requiring high safety patterns, control and assurance of products to be marketed, as is the case of those connected with the pharmaceutical industry.

The joint development of new mathematical techniques for the analysis of frequency signals permits the use of spectroscopy for the simultaneous monitoring of a high range of materials starting from just one spectre.

The—micro and macro—structure determines any material's physical behaviour, namely the mechanical properties, structural anomalies or transference/resistance against mass transference.

The density of one material is a projection of the structure thereof.

The techniques that permit the analysis of the structure are, therefore, an indispensable source of information to decide and analyse the structure of objects.

The preferred structural detector is X-Rays, with applications in the analysis of macro- and microstructures, in addition to visual analysis, including, in medical care, bone structure and other tissues or, in engineering, the inspection of buildings and structures. In these applications, the density of the analysed materials is the observed factor that simultaneously permits:

The identification of anomalies
The structural characterization
The microstructure interpretation.

There is no knowledge of industrial solutions applicable in the cork sector with the purpose of classifying and separating stoppers according to their visual or structural characteristics, except in what concerns the methods based on the use of cameras to photograph the surface thereof, the images being then processed for separation purposes.

The said industrial systems, commonly designated by the electronic choice of cork stoppers, are supplied by several manufacturers, with slight differences among the available products, especially in respect of the number and placing of the inspection cameras and of the software developed to facilitate man-machine communication.

In such equipments, the separation of stoppers in a same batch is performed according to their exterior aspect and macro porosity. Nevertheless, visual inspection by trained operators is not completely abandoned. Besides, these equipments are only partially effective in the elimination of structural defects that compromise the stopper's performance.

In the present invention, we seek the preferential industrialisation of the X-Ray analysis technique as a way of predicting, after signal processing, 1. The existence of structural defects that compromise the sealing function of the cork
2. The mass transference behaviour and, in particular, oxygen permeability.

The fact that the radiographic image has a good correlation with the average free trajectory of the structure explains, in part, the establishment of the oxygen transport regime.

Mathematical Signal Processing

The recourse to non-invasive and non-destructive methods for the acquisition of signal, as those based on the electromagnetic energy behaviour, leads to obtaining a large quantity of income data. Generally, this data base is too heavy for an algorithm of practical application and contains a large amount of redundant information which does not contribute for the acknowledgement of the product or of the process under analysis.

To compensate for such difficulty, mathematical manipulation is adopted so that it represents the information according to vectors, in a reduced/designed format. When the information extraction is performed according to carefully selected features, relevant data are obtained to perform the intended analytical task, using the strictly necessary inputs and not the too complex whole matrix of original information.

In other words, generically, the existing mathematical methods to process the spectra are based in the factorisation of spectra in a new system of bases (generally a sub-space) so that a representation with greater interpretability is obtained and those parts of the spectrum with more relevant systemic information are extracted.

This class of mathematical methods is described in great detail in the specialized literature under the topic of 'chemiometrics'. Well succeeded applications of these methods to analyse chemical information and obtain quantitative models to calibrate chemical species based on spectroscopy are scientifically well supported (some quotes).

Therefore, the feature extraction constitutes a methodology for the selection of vectors which, in practice, permit the analysis of a certain problem with interesting precision. The recourse to techniques that allow the approach of feature patterns selected from the original data basis is essential. Such techniques permit to avoid redundant information and:

1. To simplify the data to be processed;
2. To reduce the dimensions to be processed—adopting latent variables;
3. To systemize the information acquired by the spectra.

This invention describes the application of signal decomposition techniques, supervised or not, respectively and, for example, PLS (Partial Least Squares) and PCA (Principal Components Analysis), as multifarious techniques for analysing the image recorded by non-invasive and non-destructive methodology, e.g., X-Rays. In this way it is possible to reduce significantly the number of attributes to be analysed.

The strictly necessary signal for classification is extracted from the complex signal obtained from the non-invasive and non-destructive spectroscopic analysis: by applying SVD (Singular Value Decomposition) it is possible to bring out the relevant signal, although small, of the original sound.

The selection of the appropriate method for pre-processing is crucial for the final result. Another essential feature for the development of the present patent concerns the need to identify behaviour patterns that may relate to the variable to be quantified.

The data so processed supply information that allows for:
The automatic detection of objects
The calculation of interesting regions of the analysed objects for further classification.

BRIEF DESCRIPTION OF THE DRAWINGS

The following description of a preferred embodiment is based on the attached drawings on which, with no limitation intended, the following is represented.

LIST OF REFERENCE NUMBERS OF FIGS. 2 AND 3

Figure 2:
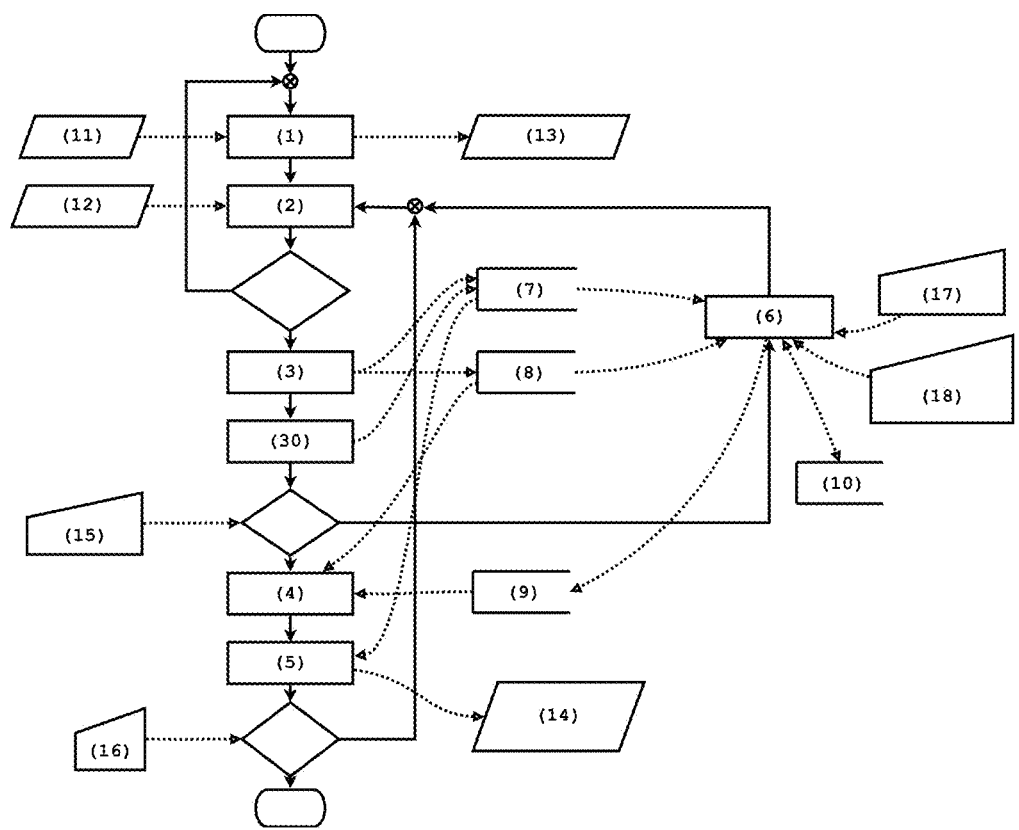
In FIG. 2, general diagram—algorithm development.

FIG. 2
Image Processing (1)
Objects Detector (2)
Objects Processing (3)
Parameter Forecast (4)
Classifier (5)
Forecast Model Updating (6)
Calculation of statistical parameters (7)
FFT and Growth Vector (8)
Forecast Model (9)
Dataset Training (10)
X-Ray Image (11)
Object Position (12)
X-Ray/Detector Calibration Parameters (13)
Object Classification (14)
Test Object (15)
Stop Command (16)
Numerical Forecast Method (17)

Figure 3:
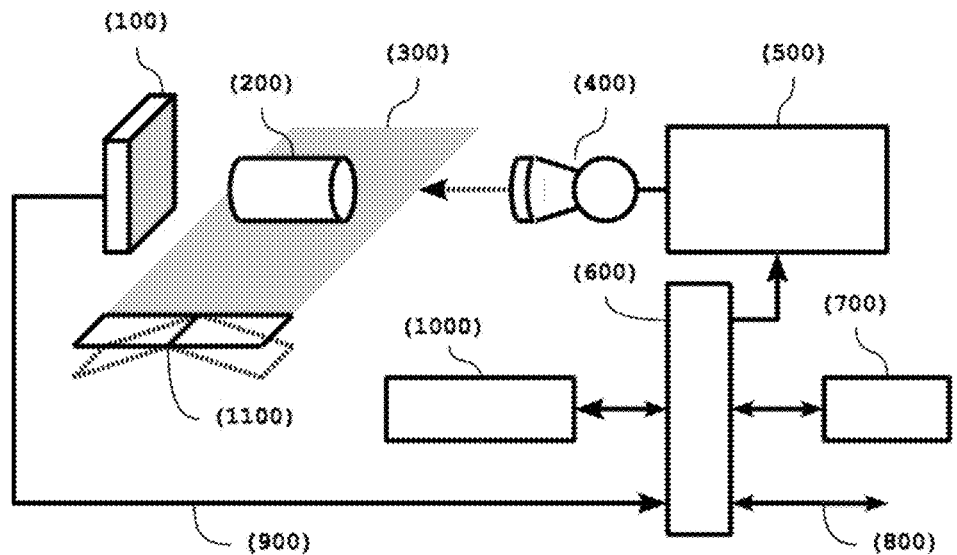
In FIG. 3, a block diagram schematically representing the equipment to carry out the method that is the object of the invention.

Supervision Laboratory Methods (18)
Defects Detector (30)
FIG. 3
X-Ray Digital Detector (100)
Stoppers (200)
Carried on the belt (300)
X-Ray transmitter tube (400)
X-Ray control unit (500)
I/O control unit (600)
Processing unit (700)
Input/output of information alien to the system (800)
Image transmission (900)
Programmable automat (1000)
Selector (1100)

Detailed Description of One Embodiment

The invention described herein combines image analysis tools with a unique and innovative solution for the classification of cork stoppers according to parameters previously selected such as gas permeability, presence of defects or density.

Figure 1:
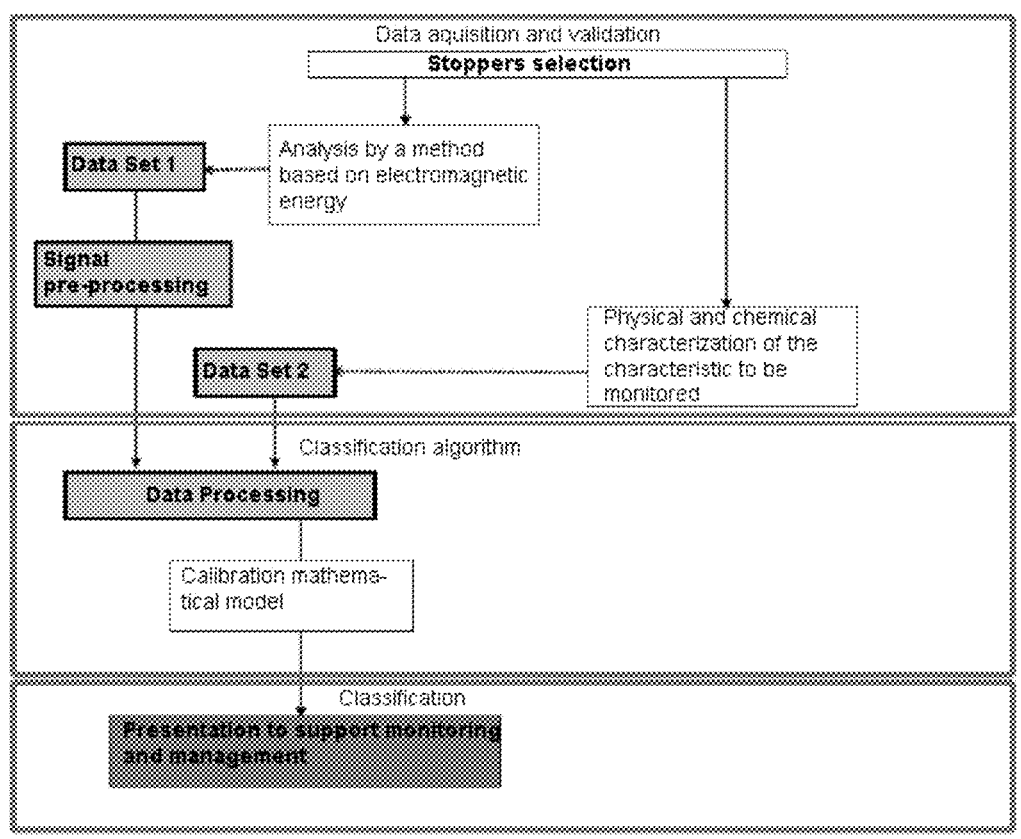
In FIG. 1, a flow chart summarizing the steps of the invention.

The method to monitor and support management of the cork stopper production is developed according to the steps represented in the flow chart shown in FIGS. 1 and 2 and detailed hereafter.

Industrialization of the process does necessarily involve:
1. The algorithm for object detection;
2. The algorithm for the detection of the growth vector on which the signal treatment is performed.

The procedure for the acquisition and validation of data presupposes the previous selection of samples representing the population intended for the mathematical model to be constructed for the later automated separation: e.g., stoppers with a determined calibre and surface treatment.

These samples are analysed according two complementary perspectives that generate two data sets (FIG. 1).

Data set 1—Analysis by means of a non-invasive and non-destructive technique, preferably X-Rays, under conditions set in advance.

After an image is extracted with the desired sensitivity the signal is processed mathematically. The projection of the structure in a plan (dimensional reduction) leads to a loss of information. The Supervision method applied to the Forecast Model attenuates this loss of information.

The application of Fourier Transform, hereafter designated as FFT, according to the cork's vector "years of growth" and maximum diameter of the object, allows for later calibration with the relevant parameters.

Figure 9:
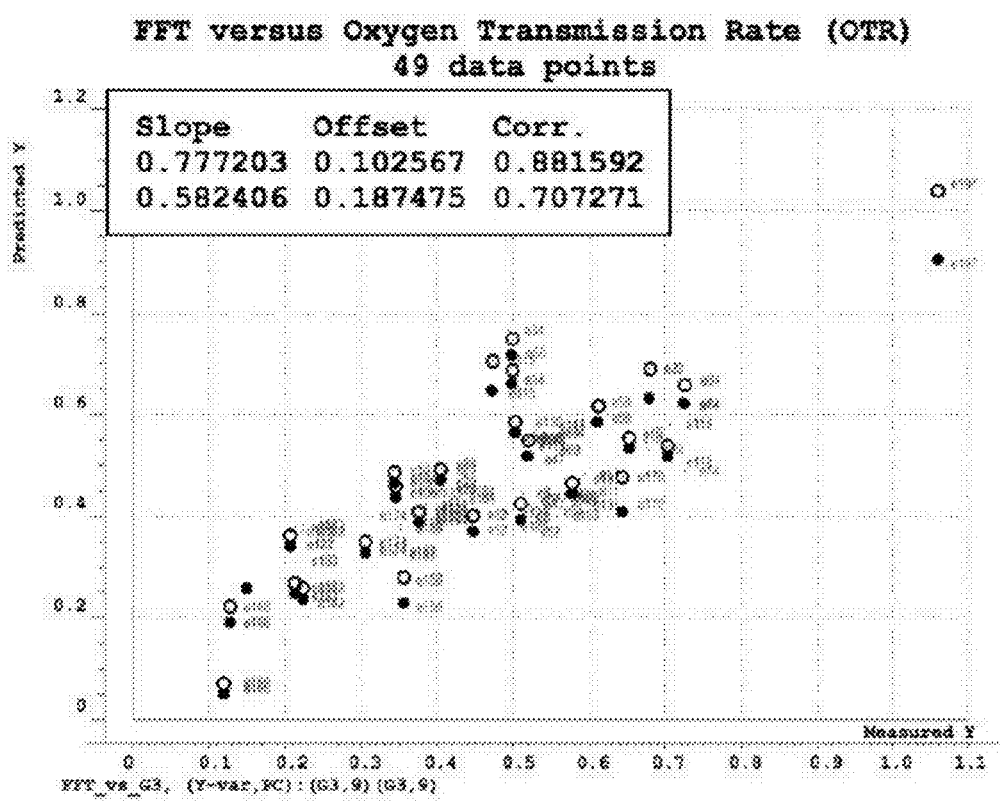
In FIGS. 9 and 10 are represented graphics of the correlation between FFT and the value of stoppers oxygen permeability.
Figure 10:
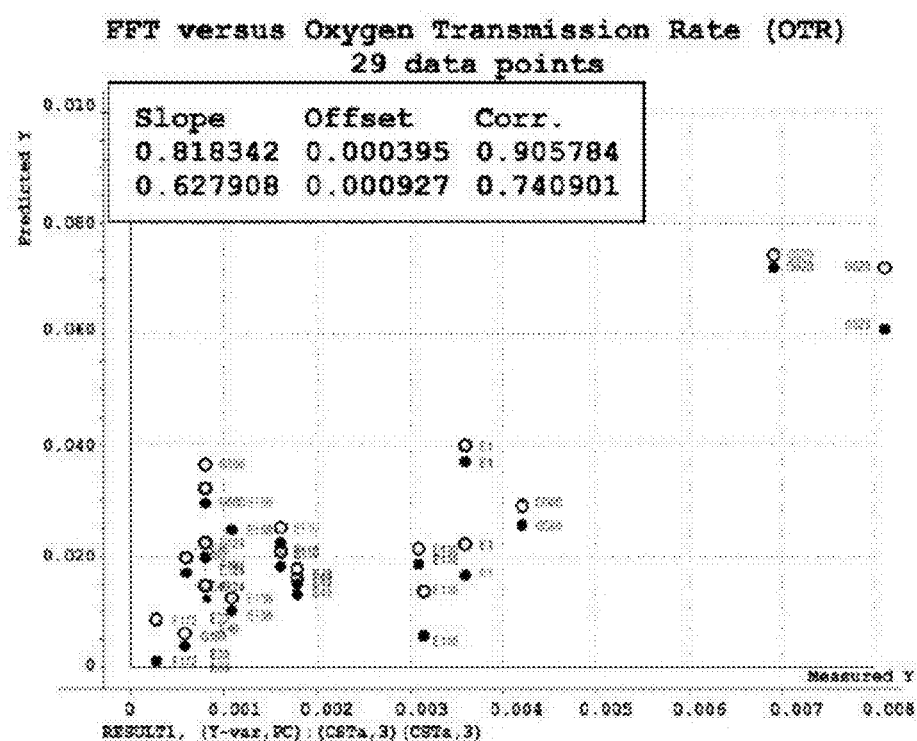

FIGS. 9 and 10 represent the correlation charts between FFT and the stoppers oxygen permeability value.

Data set 2—Acquiring of relevant parameter, e.g., gas permeability, presence of defects or density.

As it may be observed in FIG. 2, the interface components are as follows.
Inputs:
X-Ray image (11)
Object position (12)
Manual Inputs:
Test object (15). (Object to be submitted for measuring permeability by a supervision laboratory method)
Numerical Forecast Method (17)
Parameter measured by a normalised laboratory supervision method (18)
Stop command (16)
Outputs:
X-Ray/Detector calibration parameters (13)
Object classification (14)
Data Structures
Calculation of Statistical Parameters (7)
Type of defects, average values, mean, mode, standard deviation, etc.
FFT and Growth Vector (8)
Discrete Fourier Transform (approximate result) of the original image and of the growth vector. The result of Fourier transform has the same dimension and cardinals as the original and complex values. As the image values are real numbers, the result presents symmetric values. Thus, half of the matrix or vector values can be taken into account.

As the manufacturing processes of the cork stopper cannot guarantee the alignment of the phenomena under study—e.g., although similar, the patterns of two objects may be displaced—the phase information of the complex signal may be considered as neglectable.

To eliminate the phase information and considering each value of the matrix or vector in the form:

$$a+bi$$

the amplitude shall be:

$$A=\overline{a^2+b^2}$$

Forecast Model (9)
Numerical forecast model (9) obtained by supervision laboratory method. This model shall be represented by a function which, considering a determined growth vector, shall attribute a permeability value.

Data set Training (10)
Historical recording of growth vectors (obtained by the industrial method) and class attributes (obtained by the Supervision Laboratory Method).
Processes
Image Processing (1)
The function of this block is to enhance the image quality acquired from the Digital X-Ray Detector (100), correction of systematic errors, reduction of sound, improvement of contrast and normalisation.

Objects Detector (2)
Automatic algorithm to detect objects in the radiographic image. The objects positions (12) can also be pre-determined by external information. In this case, the mechanism of auto-detection is not executed.

Figure 4:
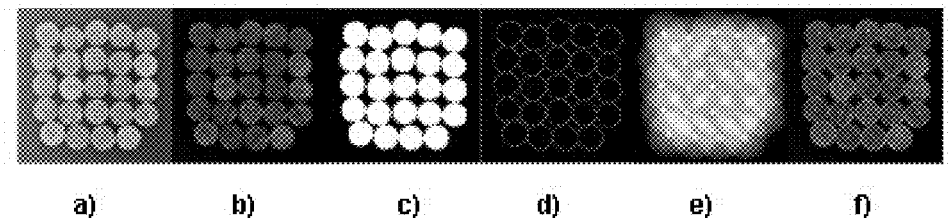
In FIG. 4, steps in the detection of objects: a—original image; b—reduction of sound, background subtraction and normalisation; c—entropy based binarization; d—contour detection; e—circles detection by Hough transform; and f—objects position and region of interest.

The objects detection algorithm in the image/streaming of the radiographic detector follows the steps shown in FIG. 4 *a-f* and presents an internal data structure that records the global coordinates of each object, ensuring that each object is unique. The position of each object is obtained by local maxima within the accumulating space generated by Hough transform.

Objects Processing (3)
Obtain relevant information, for the processing of each object, such as statistical parameters and calculation of FFT.
Defects Detector (30)
Algorithm to detect structural anomalies inside the object.
Parameter forecast (4) (e.g., permeability)
Object parameter (such as gas permeability) numerical forecast algorithm, with supervision such as PLS, according to Forecast Model.
Classifier (5)
The final classification of each object is obtained by the weight of statistical parameters and by the expected quantification of the parameter to be determined (by permeability or by the presence of defects or density, as expected).

Forecast Model Updating (6)

Laboratory method to develop and train a numerical forecast model of the parameter to be determined (e.g. permeability, presence of defects or density), with Data Mining techniques.

Equipment

As outlined in the block diagram of FIG. 3, the necessary equipment to carry out the method that is the object of the invention does essentially comprise an X-Ray transmitting tube (400) and an X-Ray digital detector (100). The stoppers (200) transported on the belt (300) pass between these two modules, and their image is acquired after digitalisation of the signal in the X-Ray digital detector (100). The image (900) transmission is sent to I/O control unit (600). Later on the image is processed and stoppers are classified in the processing unit (700) and led to different reservoirs by the selector (1100). Any input/output information alien to the system (800) is represented in the diagram by an arrow. Carrier belt (300) and selector (1100) are driven by the programmable automat (1000).

Method Description

We can subdivide the system in two autonomous and concurrent processing blocks: The inspection and classification industrial process and the laboratory process.

The classification process corresponds to steps (1) to (5) (FIG. 2) and pretends to have a real time performance. "Real time" is meant to be a process abiding by time constraints according to the time constant values of the associated process. "Associated process" would be the industrial production of cork stoppers.

The process receives an image or a video streaming from the X-Ray digital detector (100). The X-Ray control unit (500) may send some calibration information (13) from a previous image processing (1).

Then, the detection of new objects (2) and the calculation of statistical parameters (7) that are relevant for study.

By means of an external command a determined test object (15) may be led to laboratory examination. After the laboratory examination of the supervision method (18) is performed to obtain the class attribute of a determined object, the training data set (10) and the forecast model (9) are updated by the forecast model (6) updating process.

After predicting the parameter (4), in this case permeability, having recourse to data structure and to forecast model (9), the final classification of the object (5) is obtained by adding the structure information (types of defects, density, statistical parameter, etc.) The presented final classification of the object (14) is transmitted to the programmable automat (1000) to drive the selector (1100).

Then, if the stop command (16) is not active, an order is sent to the automat to drive the carrier belt (300) and restart the algorithm for the image processing process (1).

Supervision Laboratory Methods (18)

To measure the parameter according to which the categorisation of the objects is pretended standard industrial or laboratory methods are used.

In the case of oxygen permeability, different methods may be adopted, the following being exemplary:

Electrochemical
Colorimetric
Luminescence based
With zirconium or micro GC sensors
Based on the promotion of oxygen reaction with other molecules

EXAMPLES

I—Defects Detection

Figure 7:
In FIG. 7, an example of the image segmentation for highly shiny regions, a—original image, b—image binarization for very bright regions.

FIG. 7 shows an example of a radiographic image of a cork stopper. The more visible particularity is the growth pattern. However, this is not the most interesting phenomenon in this phase but rather the anomalies, which do not present a regular pattern.

The identification of the defects in the object is obtained by segmentation of the image histogram in a very bright region, regular pattern region and low brightness region. The image segmentation dots are obtained by entropy criteria, which permit to achieve optimum histogram segmentation dots and minimise the number of false positives.

The recognition of different brightness regions is directly related to the potential quantification of one defect, which is the result of significant and intense differences in density.

II—Determination of Mass Density Starting from Optical Density

This example demonstrates the possibility of determining mass density, a parameter resulting from the cork macro and micro structural characteristics, starting from the image obtained by exposure of the plant tissue to an X-Ray detection system.

The critical parameters of optimisation to obtain the analytical signal, the average brightness of the X-Ray generated image, are the following:

Starting from the X-Ray analysis
Power (A)
Voltage/Current (V)
Distance to the object (m)
Exposure time (s)

This step was essential to confirm the adequacy of the technique to the intended analysis. The strong correlation between optical density and sample density supports the technique's feasibility.

1. Equipment Calibration

Signal acquisition parameters: Power; Voltage; Distance and Time:

The following X-Ray equipment (trademark Philips), equipped with a digital detector of 200×300 mm, was used to obtain the image. The pattern curve is obtained using aluminium foil of different thicknesses. Within a thickness range of 0.8-1.2 mm this material presents an optical density similar to the plant material cork.

In parallel, employing the optimisation first cycle parameters, X-Ray images of stoppers of different classes are acquired.

The initial parameters were Power=100 mA; Voltage=40 kV; Distance=1 m and Time=0.1 sec.

Image Digitalisation Parameters

Figure 5:
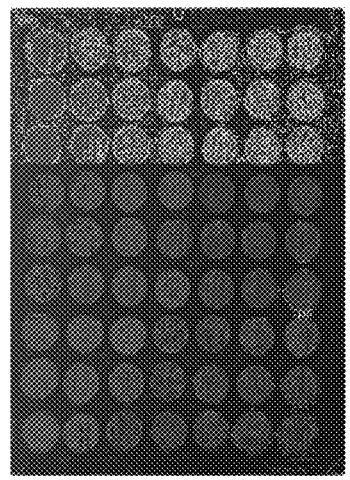
In FIG. 5, an X-Ray image obtained after digitalisation of the signal acquired in the detector.
Figure 6:
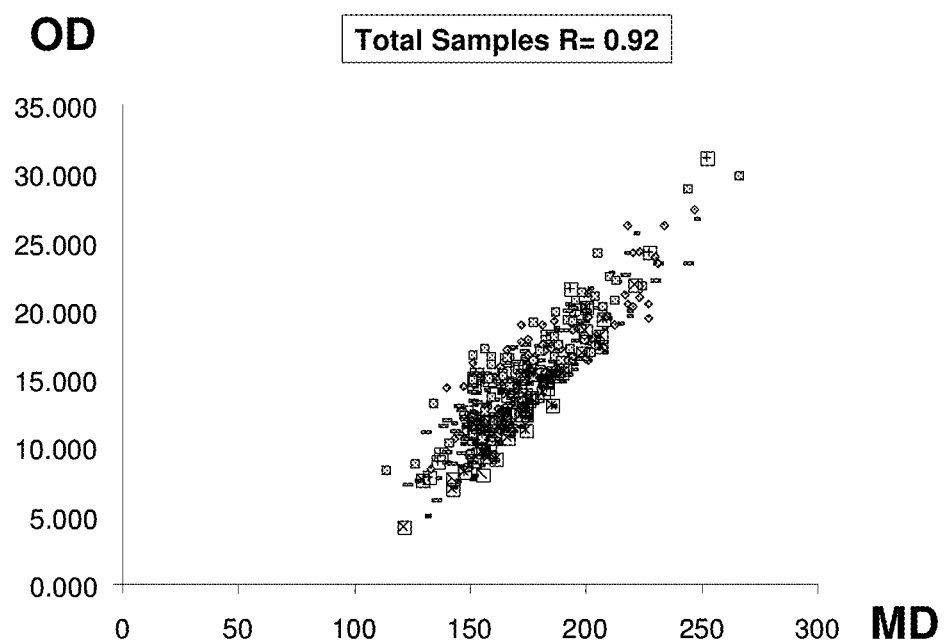
In FIG. 6, the detector's calibration curve.

X-Ray images are obtained after digitalisation of the X-Ray signal captured in the detector. The digitalisation import parameters were GA=0.9; GS=0.5; s=70; L=2.0. The image corresponding to each pattern is then imported using the Software Image J (see FIG. 5).

The curve is then determined by placing the aluminium foil thickness in the abscissa and the calculated average brightness of the image in the ordinate using the maximum area thereof.

The process is interactively repeated until a linear curve is obtained with a higher correlation coefficient r>0.9.

In parallel, some different X-Ray images were acquired from different samples of stoppers of different classes.

Then, the object's (stopper) average brightness is determined and the equivalent in aluminium thickness is obtained by interpolation.

Compatibility between Images–Normalisation

Using the foil which resistance to the X-Ray transference is immediately lower than that of the material under study, cork, the brightness of the image background is adjusted calculating the total image mode by adjusting to a value common to the whole image.

The image normalisation is performed by adjusting the brightness of the image under study to a pre-established value.

Elimination of Systematic Errors in the Image

The acquisition of the radiographic image is accompanied by some deviations caused by factors that may be considered as systematic: The bulb temperature variation, the spatial non-uniformity of the digital sensor's sensitivity, etc.

To eliminate the aforementioned we chose the aluminium foil image which resistance to X-Ray transference is immediately lower than that of the image mode under study and the two were subtracted.

Aluminium Subtraction

The final correction of the image is effected by subtracting the respective images: X-Ray image of the stoppers (9 per 7 objects) less 0.8 mm aluminium background.

The stoppers are horizontally placed on a matrix previously referenced for later identification; column of 7 objects per line of 9 objects.

The calibration curve of the detector was determined with five patterns prepared as follows: pP2 mm, 2 mm aluminium foil; Pp4 mm, one 4 mm aluminium foil; Pp6 mm, one 2 mm aluminium foil covered by a 4 mm foil; Pp8 mm, two overlapping aluminium foils; Pp10 mm, two 4 mm foils and one 2 mm foil. Thus, 32 aluminium foils 20.8 mm thick and 32 4 mm 1.6 foils were used.

III—Permeability

The following examples concern the methodology development to predict the stoppers oxygen permeability.

As a supervision laboratory method (18) (FIG. 2) was used the determination of oxygen permeability, as represented in the graphics of FIGS. 9 and 10, per equipment, abiding by ASTM norms.

The obtained results are shown at the end of this example's description.

Growth Vector and Permeability Forecast

As formerly described, the radiographic image is acquired. The predominant pattern in the radiographic image of the cork stopper is the natural growth pattern. Such pattern does also have the characteristic of varying essentially in one direction. Therefore, we can represent that pattern with one vector which is designated herein by Growth Vector.

Thus, such vector may be a representation of the mechanical characteristics of the cork stopper wherein, in addition to the regular cork growth, any possible anomalies during that growth are shown.

Figure 8:
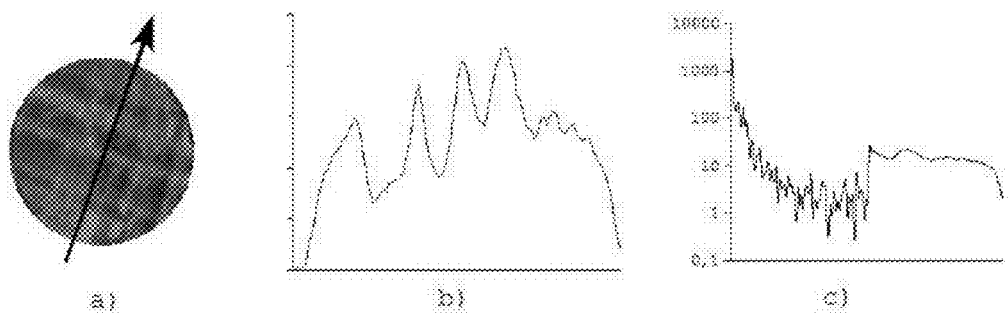
In FIG. 8, steps to obtain growth vector FFT, a—growth vector, b—growth vector values (grey levels of the image), c—discrete Fourier transform (logarithmic scale)

Starting from the direction of the lines formed by the growth pattern, the perpendicular line passing through the centre of the circle thereof is calculated. The Growth Vector is thus obtained (FIG. 8).

The permeability forecast is obtained on the basis of the Growth Vector's FFT.

The results obtained and presented in the following examples and figures show a high correlation between FFT (FIGS. 9 and 10) and the very permeability value measured with the supervision method (18) described in the algorithm (see in the diagram the algorithm summary of FIG. 2).

Samples of natural cork stoppers were prepared in this example and submitted to:

X-Ray analysis followed by the image processing described in this patent;

Determination of the permeability by standard methods.

BIBLIOGRAPHY

ASTM F 1307-02; "Standard method for oxygen transmission rate through dry packages using a coulometric sensor"; EDT 2006

Casey, J.; "Venting or Leaking? Residual Headspace Pressure in Bottled Wines"; The Austr. Grapegrower & Winemaker, Volume 453, pages 115-118 (2001)

Crochiere, G. K.; "Measuring Oxygen Ingress During Bottling/storage". Practical Winery & Vineyard, January/February 2007

Eleanor & Ray; "Heald Getting Closure. The continuing search for the best way to seal the bottle"; wine.appellationamerica.com/wine-review, Jan. 18, 2008

Ferreira, A. C. et al.; "Identification of key Odorants related to the typical aroma of oxidation-spoiled white wines"; J. Agric. Food Chem. 2003, 51, 1377-1381

Ferreira, A. C. et al.; "Kinetics of oxidative degradation of white wines and how they are affected by selected technological parameters"; J. Agric. Food Chem. 2002, 50, 5919-5924

Hart and Kleinig; "The role of oxygen in aging of bottled wine"; The Australian & New Zealand Grapegrower & winemaker, 2005

Kwiatkowski, M. J. et al; "The impact of closures, including screw cap with three different headspace volumes, on the composition, colour and sensory properties of a Cabernet Sauvignon wine during two years' storage"; Australian Journal of Grape and Wine Research, 13, 2007

Lopes, P. et al. "Impact of storage position on oxygen ingress through different closures into wine bottles," Journal of Agricultural and Food Chemistry, 2006, 54(18), 6741-6746

Lopes, P. et al. "Non-destructive colometric method to determine the oxygen diffusion rate through closures used in winemaking," Journal of Agricultural and Food Chemistry, 2005, 53, 6967-6973

Phillips, C.; "Recent Research: The Science of Closures," From Wine Business Monthly, Sep. 15, 2005; WBM, September 2005, www.winebusiness.com Tran, T., et al.; "Using Membrane Technology to Optimise Closure Performance". The Australian & New Zealand Grapegrower & Winemaker, March 2007

Tudor, P.; "Is This The Closure For Your Wine An in-depth look at the pros and cons of wine development under screw caps." Wine Business Monthly—July 2005

Waters, L., et al.; "Wine and Oxygen Research at the AWRI", January 2008, Sacramento Patent WO 2007/026233 A2; Method and System of Multivariate Analysis on Slice-wise data of reference structure Normalised Images for Improved Quality in Positron Emission Tomography Studies

The invention claimed is:

1. A non-destructive and non-invasive method for inspecting plant materials via electromagnetic radiation in order to selectively and automatically separate the plant material based on one or more parameters of said plant material, said method comprising a calibration phase and a classification phase, wherein the calibration phase comprises:
(i) acquiring, via an x-ray transmitting tube and an x-ray detector, a signal corresponding to a radiographic image of one or more sample objects, said sample objects corresponding to said plant material;
(ii) automatically detecting, via a processor unit, the one or more sample objects in the signal corresponding to the radiographic image;
(iii) calibrating one or more parameters of said one or more sample objects, wherein said calibration comprises:
  (a) determining, based on said signal corresponding to a radiographic image of said one or more sample objects, a growth vector;
  (b) transforming, via Fourier transformation, said growth vector into at least one growth vector value;
  (c) quantifying at least one parameter, wherein said at least one parameter comprises oxygen gas permeability or mass density of said plant material; and
  (d) obtaining a forecast model corresponding to the at least one transformed growth vector value of said one or more sample objects versus said at least one parameter of said one or more sample objects; and
wherein the classification phase comprises repeating steps (i) to (iii) b) for a test object to be inspected, of a plant material and further comprises:
(iv) processing, via the processor unit, a signal corresponding to a radiographic image of said test object to be inspected in real time, said processing comprising; the determination of a parameter comprising oxygen gas permeability or mass density of said test object, based on the forecast model obtained in the calibration phase and the growth vector value determined in step (iii) b) of the classification phase; and
(v) categorizing said test object to be inspected according to said parameter determined in step (iv).

2. The non-destructive and non-invasive method to inspect plant materials according to claim 1, wherein the forecast model is constructed based on one or more sample objects previously selected from the following variables:
  a matrix containing values of said one or more parameters, comprising oxygen gas permeability or mass density determined in the calibration phase; and
  a matrix containing values obtained from one or more signals respectively corresponding to one or more radiographic images of said one or more sample objects.

3. The non-destructive and non-invasive method to inspect plant materials according to claim 1, wherein the plant material is cork material.

4. The non-destructive and non-invasive method to inspect plant materials according to claim 1, wherein the plant material comprises cork stoppers.

5. The non-destructive and non-invasive method to inspect plant materials according to claim 1, wherein categorizing said test object further comprises:
  rejecting a test object to be inspected having said parameter not complying with said forecast model;
  accepting a test object to be inspected having said parameter complying with said forecast model; and
  categorizing said accepted test object.

6. Equipment configured to carry out the method according to claim 1, comprising:
  an X-Ray transmitting tube and an X-Ray digital detector through which said one or more sample objects or test object to be inspected are carried by a carrier belt thereby obtaining said signal corresponding to said radiographic image of each of said one or more sample objects or test object to be inspected;
  an I/O control unit, configured to receive transmission of the radiographic image;
  a processor unit configured to perform steps (ii), (iii)(a), (iii)(b), (iii)(d), (iv) and (v);
  input means to input the at least one parameter of step (iii)(c) in said processor unit;
  a selector configured to select one or more sample objects and lead the selected sample objects to two or more different reservoirs, according to the result of step (v);
  a programmable automat configured to operate the carrier belt and the selector.

* * * * *